US007252746B2

(12) United States Patent
Schaeffer

(10) Patent No.: US 7,252,746 B2
(45) Date of Patent: Aug. 7, 2007

(54) ELECTROPOLISHING APPARATUS AND METHOD FOR MEDICAL IMPLANTS

(75) Inventor: Darin G. Schaeffer, Bloomington, IN (US)

(73) Assignee: Cook Incorporated, Bloomington, IN (US)

( * ) Notice: Subject to any disclaimer, the term of this patent is extended or adjusted under 35 U.S.C. 154(b) by 466 days.

(21) Appl. No.: 10/712,420

(22) Filed: Nov. 12, 2003

(65) Prior Publication Data

US 2005/0098444 A1    May 12, 2005

(51) Int. Cl.
*B23H 9/04*   (2006.01)
*C25F 3/16*   (2006.01)
(52) U.S. Cl. ............... 204/224 M; 204/212; 204/217; 204/242; 204/272; 205/640
(58) Field of Classification Search ............... 204/242, 204/196.38, 212, 218, 224 M, 228.6, 217, 204/272; 205/640–644, 654, 655
See application file for complete search history.

(56) References Cited

U.S. PATENT DOCUMENTS

| | | | |
|---|---|---|---|
| 3,935,085 A * | 1/1976 | Baker et al. ............... 204/474 |
| 4,038,702 A | 8/1977 | Sawyer ............... 3/1.5 |
| 4,065,816 A | 1/1978 | Sawyer |
| 4,080,706 A | 3/1978 | Heilman et al. |
| 4,132,618 A * | 1/1979 | Boulanger et al. ........... 204/218 |
| 5,145,474 A * | 9/1992 | Moore ............... 482/51 |
| 5,378,331 A | 1/1995 | Kemp |
| 5,746,691 A | 5/1998 | Frantzen |
| 5,788,558 A | 8/1998 | Klein |
| 5,891,507 A | 4/1999 | Jayaraman |
| 6,086,455 A | 7/2000 | Frantzen |
| 6,183,353 B1 | 2/2001 | Frantzen |
| 6,275,826 B1 | 8/2001 | Geiner et al. ............... 707/101 |
| 6,299,755 B1 | 10/2001 | Richter ............... 205/651 |
| 6,315,885 B1 | 11/2001 | Hocheng |
| 6,375,826 B1 | 4/2002 | Wang et al. |
| 6,537,202 B1 | 3/2003 | Frantzen |
| 6,599,415 B1 | 7/2003 | Ku et al. |
| 6,679,980 B1 | 1/2004 | Andreacchi ............... 204/272 |

(Continued)

FOREIGN PATENT DOCUMENTS

EP    1 369 099 A2    12/2003

(Continued)

OTHER PUBLICATIONS

Publication, "Electro Glo Case History, Electro Glo deburrs 3300 holes in 30 minutes," Electro Glo Company, 625 S. Kolmar Ave., Chicago 24, Ill. (2 pages).

(Continued)

*Primary Examiner*—Roy King
*Assistant Examiner*—Lois Zheng
(74) *Attorney, Agent, or Firm*—Brinks Hofer Gilson & Lione

(57) ABSTRACT

An electropolishing apparatus and method are provided for polishing stents and other medical implants. The apparatus includes a motor that rotates a roller. The roller continuously rotates the medical implant to be electropolished. One of the advantages of the apparatus and method is that marks generated around the electrical contact between the anode and the medical implant are minimized. In addition, the medical implant is polished more evenly than conventional electropolishing systems.

6 Claims, 3 Drawing Sheets

U.S. PATENT DOCUMENTS

| | | |
|---|---|---|
| 2002/0007209 A1 | 1/2002 | Scheerder et al. |
| 2002/0092583 A1 | 7/2002 | Pelton et al. |
| 2002/0198593 A1 | 12/2002 | Gomez et al. |
| 2003/0113478 A1 | 6/2003 | Dang et al. |
| 2003/0143315 A1 | 7/2003 | Pui et al. |
| 2005/0197689 A1 | 9/2005 | Molaei ............... 623/1.13 |

FOREIGN PATENT DOCUMENTS

| | | |
|---|---|---|
| JP | 59205220 | 11/1984 |

OTHER PUBLICATIONS

Jumer, John F., "Electropolishing: What, How and Why," Electro Glo Company, 621-625 S. Kolmar Ave., Chicago 24, Ill. (3 pages), Reprinted from *Metal Finishing*, Aug. 1958.

Technical Bulletin, "Electro Glo "20 0", Electropolishing Concentrate for Copper and Copper Alloys," Electro Glo Co., 621 S. Kolmar Ave., Chicago 24, Ill. (4 pages).

Advertising, "Do you know why Electro Glo is *The* Specialist in electropolishing," Electro Glo Company, 625 S. Kolmar Ave., Chicago 24, Ill. (1 page).

Seabright, Lawrence (Electro-Glo Company, Chicago, Illinois), "Electrodeburring Solves Difficult and Costly Problem," (2 pages), Reprinted from the Nov./Dec. 1965 issue of *Cutting Tool Engineering*.

Advertising, "Only Electro Glo Offers You . . . ," Electro Glo Company, 625 S. Kolmar Ave., Chicago 24, Illinois. (1 page).

Publication, "What is Electropolishing," Electro Glo Company, 625 S. Kolmar Ave., Chicago 24, Illinois. (1 page).

Publication, "Only Electro-Glo Offers ALL these metal finishing features!," Electro Glo Company, 625 S. Kolmar Ave., Chicago 24, Illinois. (1 page).

Publication, "Electro Glo deburrs the hidden teeth on a Hadley cluster gear . . . ," Electro Glo Case History, Electro Glo Company, 625 S. Kolmar Ave., Chicago 24, Illinois. (1 page).

Publication, "Electro Glo goes in the hole for precise micro-inch improvement," Electro Glo Case History, Electro Glo Company, 625 S. Kolmar Ave., Chicago 24, Illinois. (1 page).

International Search Report from corresponding PCT application No. PCT/US2004/037164 dated May 4, 2005, 3 pages.

\* cited by examiner

ELECTROPOLISHING APPARATUS AND METHOD FOR MEDICAL IMPLANTS

BACKGROUND

The present invention relates generally to medical devices and particularly to electropolishing medical implants.

Electropolishing is a widely used manufacturing process that provides a smooth surface finish to metallic parts. Typically, electropolishing is used after various forming operations, such as machining, punching, laser cutting, and electrodischarge cutting, to remove burrs, sharp edges and other rough features that are generated during the manufacture of metallic parts.

The basic concepts of electropolishing are well known to those in the art, and thus, only a brief summary is required here. Conventional electropolishing processes involve contacting a metallic part with an anode (i.e., a positively charged electrode) and spacing a cathode (i.e., a negatively charged electrode) away from the metallic part. The metallic part, along with the anode and cathode, are then immersed in a bath of electrolytic fluid. Next, a voltage is applied across the anode and the cathode for a period of time. The effect of this is that metal from the metallic part is drawn away from the metallic part and is drawn to the cathode. (Although different in some respects, electropolishing may be thought of conceptually as the opposite of electroplating.) Because burrs and sharp edges experience a higher current density than smoother surfaces on the part, metal is removed from these areas at a faster rate than the rest of the metallic part. Thus, electropolishing processes leave a smooth surface finish in which the rough edges of the metallic parts are removed.

One application in which electropolishing is particularly useful is for finishing endovascular stents and other medical implants. Medical implants require exceptionally smooth surfaces since any rough edges may cause tissue irritation during or after being implanted into a person's body. Some of the medical problems that may be encountered when rough edges are not properly removed from a medical implant include inflammation, bleeding and/or scarring of the surrounding tissues. In the case of endovascular stents, such conditions can be particularly harmful and dangerous. For example, one risk that may result from the use of stents with rough edges is restenosis. Restenosis refers to the re-narrowing of a vessel which sometimes occurs after balloon angioplasty procedures. Although restenosis may occur for a number of reasons, tissue irritation and disturbance caused by rough edges on a stent may be one cause of restenosis.

Various apparatuses for electropolishing stents have been tried.

One such apparatus involves wrapping a platinum wire (i.e., the anode) around the outer surface of the stent. The stent is then lowered into an electrolytic both in a horizontal orientation (i.e., with the two ends of the stent being positioned at approximately the same height above the bottom of the bath). The cathode is formed as a single horizontal loop that surrounds the stent (i.e., the loop defines a plane that is approximately parallel to the bottom of the bath).

This apparatus suffers from several problems, however. One problem is that marks are generated on the surface of the stent around the points of electrical contact between the platinum wire and the stent. This is a common problem with electropolishing apparatuses and is not limited to the particular electropolishing apparatus described here. This problem occurs because the area of the stent located near the electrical contact between the wire and the stent experiences a higher current density than the rest of the stent. As a result, metal is drawn away from this area of the stent at a particularly aggressive rate. In addition, the wire effectively masks the portion of the stent which is in direct contact with the stent, thus creating an area that experiences a minimal rate of metal removal. The result of this arrangement is that small grooves, pits and other marks are formed around the electrical contact in a random pattern. Thus, the smooth surface finish which is desired across the entire stent is not achieved due to the marking that occurs around the electrical contact.

Another problem with this apparatus is that the metal removal rate is not uniform across the entire stent. One problem is that the ends of the stent generally experience a higher metal removal rate than the center. This is caused in part by the closer proximity of the ends of the stent to the cathode. In contrast, the center region of the stent is located at or near the center of the cathode loop (i.e., farther away from the cathode loop itself). In addition, since the anode (i.e., the platinum wire) is wrapped around the outer surface of the stent, the inner surface of the stent experiences a lower metal removal rate than the outside surface of the stent. In addition, because the anode (i.e., the platinum wire) is wrapped around the outer surface of the stent, the inner surface of the stent may experience a lower metal removal rate than the outside surface of the stent.

Uneven metal removal is a problem that many electropolishing apparatuses suffer from. In the case of stents, this problem can make manufacturing more difficult and expensive since manufacturing tolerances need to be especially tight in order to ensure proper performance of the stent. Thus, in electropolishing processes in which the metal removal rate varies significantly across the stent, the percentage of manufacturing rejects may be higher, thereby raising costs.

Other typical electropolishing apparatuses include tree-like racks having a vertical center-stem and angled arms extending out from the center-stem. Stents are installed on each of the arms by sliding the stent over an arm so that the arm extends through the cylindrical cavity of the stent. Therefore, the tree-like rack functions as the anode by contacting the inner surface of the stent. The cathode may be a cathode like that previously described or may be a metal container that holds the electrolytic fluid.

This apparatus, however, suffers from problems that are similar to those already described. For example, marking around the electrical contact between the anode and the stent may also be a problem with this apparatus. In addition, the diameter of the arm that extends through the center of the stent typically fills most of the center cavity of the stent. The reason for this is that the arms usually need to be built strong to avoid deforming the arms during loading, unloading and normal manufacturing use. The problem with this design is that the large diameter of the arms prevents electrolytic fluid from circulating within the interior of the stent. As a result, the interior surfaces of the stent do not receive a consistent polish.

It is apparent to the inventor that an apparatus and method for electropolishing medical implants is desired in which marking of the medical implant is minimized and metal removal is more consistent. Accordingly, a solution is described more fully below which solves these and other problems.

SUMMARY

A method and apparatus are provided for electropolishing medical implants and stents. The method involves continuously rotating a stent while applying a voltage across an anode and a cathode. The electrical contact between the anode and the cathode thereby continuously changes. This leads to a reduction in marks that are traditionally generated around the anode-stent contact. In addition, the apparatus provides a more uniform polishing of the stent. Additional details and advantages are further described below.

BRIEF DESCRIPTION OF SEVERAL VIEWS OF THE DRAWINGS

The invention may be more fully understood by reading the following description in conjunction with the drawing in which.

DETAILED DESCRIPTION

Figure 1:
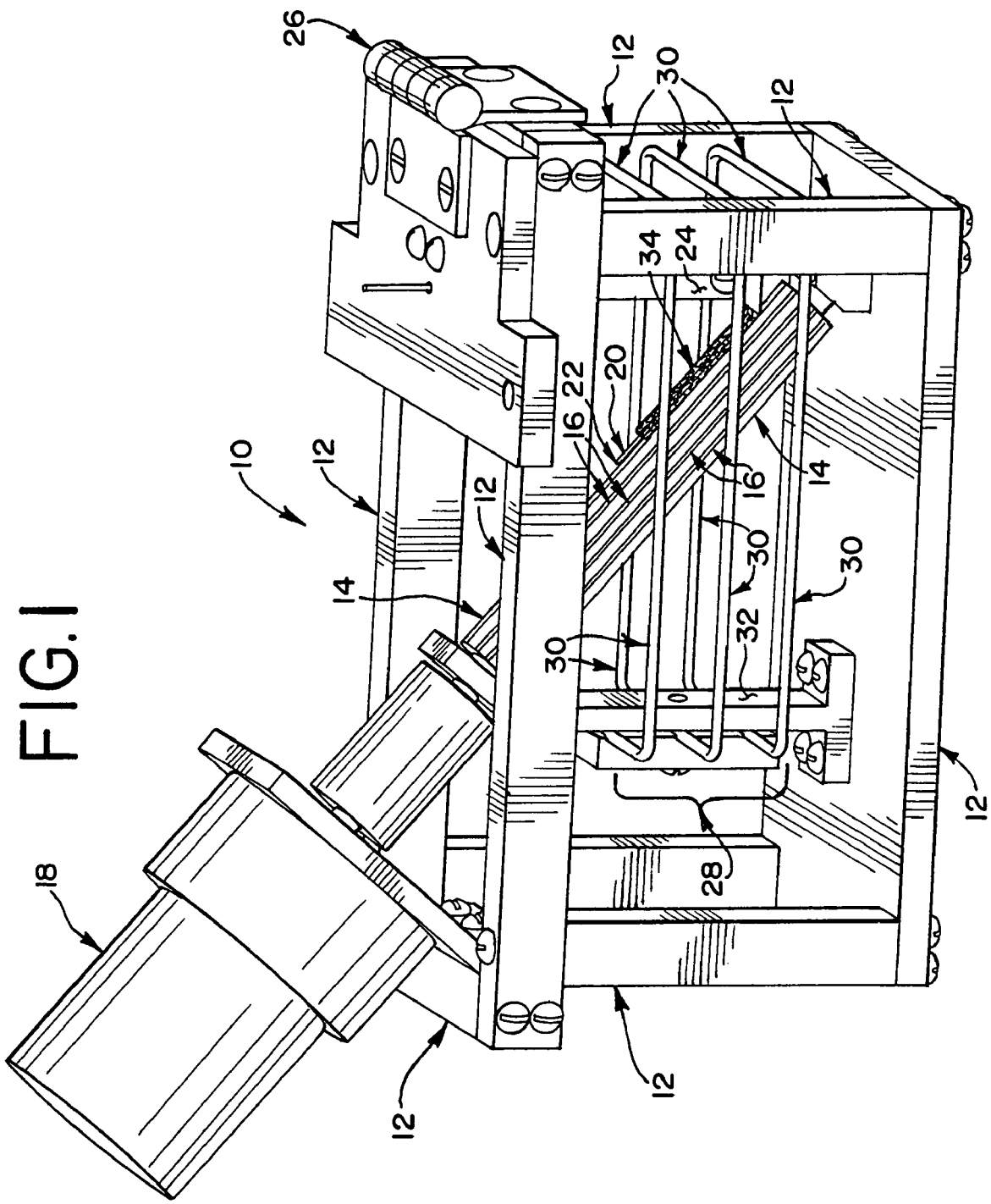
FIG. 1 is a perspective view of an electropolishing apparatus.
Figure 2:
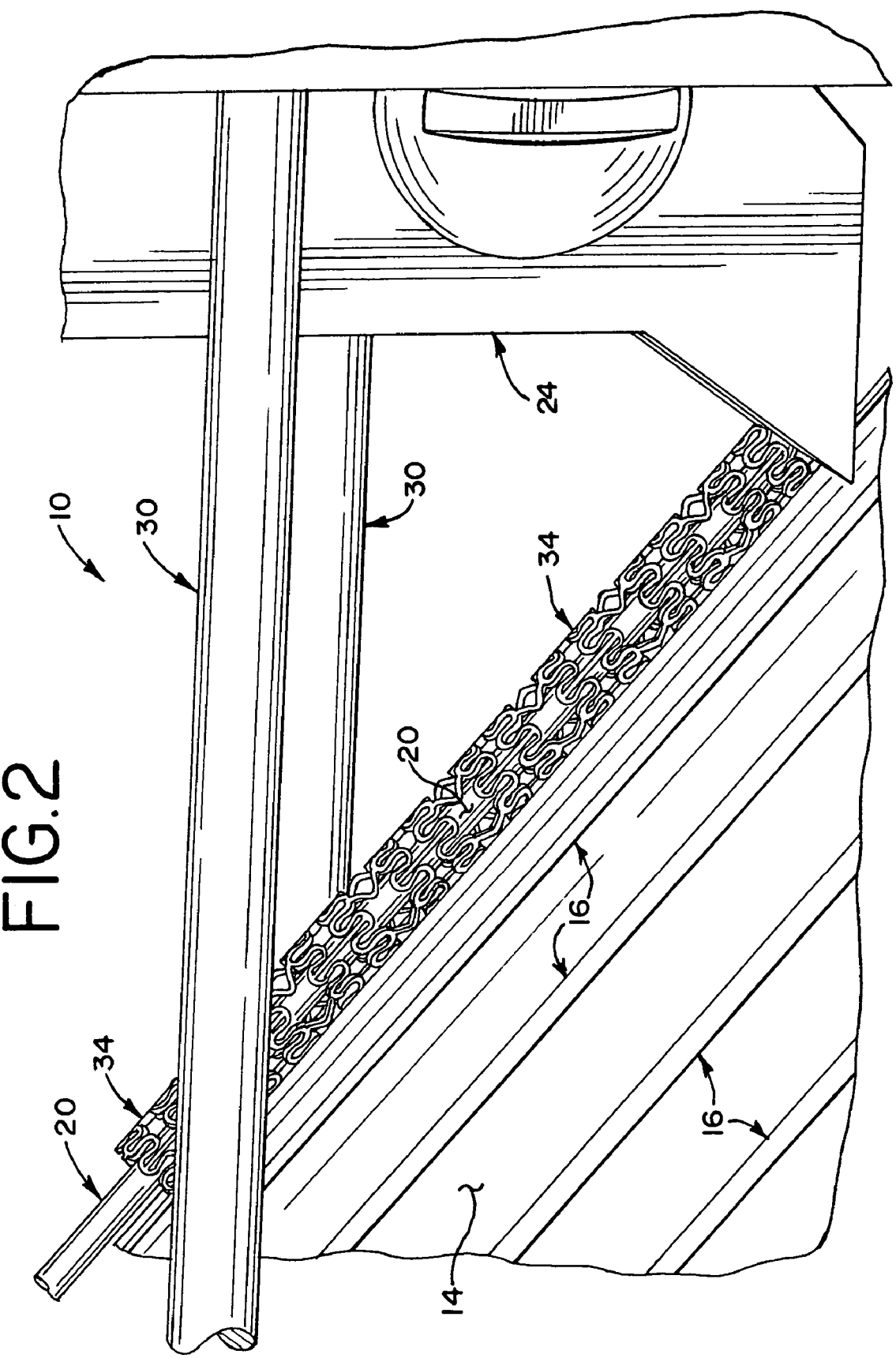
FIG. 2 is a close-up perspective view of the electropolishing apparatus.
Figure 3:
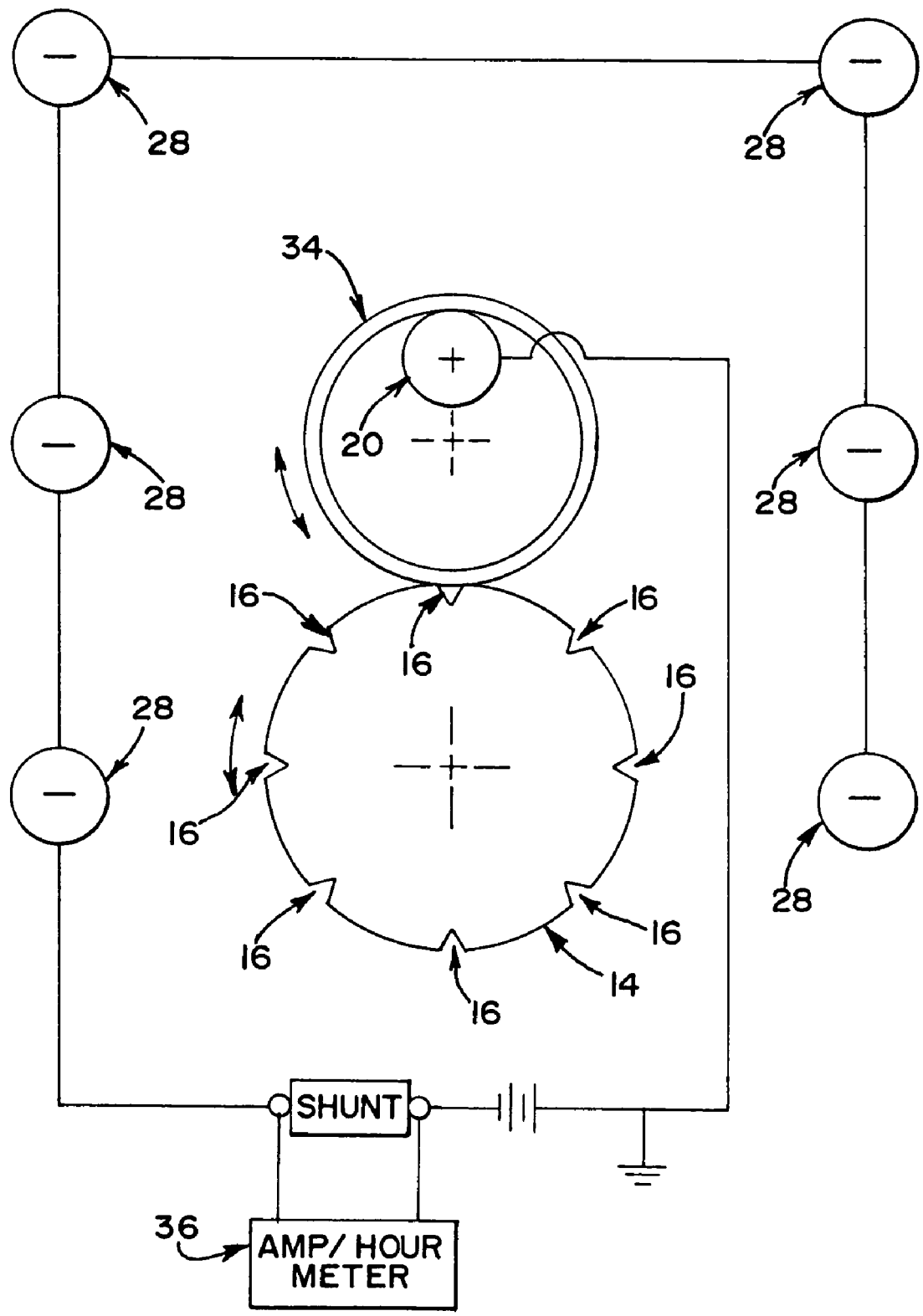
FIG. 3 is a schematic view of the electropolishing apparatus, showing an electrical circuit and an amp-hour meter.

Referring now to the drawings, an electropolishing apparatus 10 is provided. The electropolishing apparatus 10 includes a frame 12 that supports the various components of the electropolishing apparatus 10. Although numerous types of frames may be used, the frame 12 which is shown is an open frame 12 made of high density polyethylene. The electropolishing apparatus 10 is designed to be immersed in an electrolytic bath up to the top of the frame 12. The electrolytic fluid freely passes through the open frame 12 and around the various components of the electropolishing apparatus 10 except the motor 18. Alternatively, other frames may be used, such as a closed frame that also defines a container for the electrolytic bath.

The electropolishing apparatus 10 further includes a roller 14 which is rotatably mounted within the frame 12. The roller 14 is mounted in the frame 12 at an angle between a vertical orientation and a horizontal orientation. The roller 14 is made from a non-conductive material, such as high density polyethylene. Along the outer surface of the roller 14, longitudinal grooves 16 are provided which extend parallel to the rotational axis of the roller 14.

An anode 20 is mounted within the frame 12 and is spaced away from the roller 14 and oriented parallel thereto. The anode 20 is preferably a platinum wire 20 that is about 0.025 inch in diameter. Platinum is preferred since platinum does not degrade during typical electropolishing processes. In order to provide sufficient stiffness, a high strength grade of platinum may be used, such as cold worked platinum. The top end of the anode wire 20 is a free end 22, while the bottom end of the wire 20 is attached to the bottom of a swing arm 24. The wire 20 extends up through the swing arm 24 and is attached to a positive electrical charge, or other voltage potential. Preferably, the swing arm 24 is made of high density polyethylene. The swing arm 24 is attached to the top of the frame 12 by a hinge 26. Thus, the swing arm 24 and the anode wire 20 may be rotated upward out of the frame 12 around the hinge 26.

The cathode 28 includes three separate cathode loops 30. However, other arrangements for the cathode are also possible, such as more or fewer cathode loops 30, a solid plate, a wire mesh, or a metal container for the electrolytic bath. In general, the cathode must be constructed to assure sufficient current flow from the anode 20 and stent 34 to the cathode 28. Preferably, the cathode loops 30 are made from the same material as the medical implant to be electropolished in order to avoid contamination during electropolishing. Since the stent 34 described below may be made from 316L stainless steel, the cathode loops 30 may also be made from 316L stainless steel. The stent 34 and cathode 28 could also be made of other metal alloys, such as L605, MP35N, NiTi, or any other metal alloy that is commonly electropolished to improve surface finishes. The cathode loops 30 each extend around the roller 14 and the anode wire 20. The cathode 28 (represented by a bracket encompassing the three cathode loops 30) may or may not wrap all the way around the roller 14 and the stent 34. The cathode loops 30 are attached to a support post 32 that extends up from the bottom of the frame 12. The cathode 28 is electrically connected to a negative electrical charge, or other voltage potential.

A typical method of operating the electropolishing apparatus 10 follows. The electropolishing apparatus 10 is lowered into an electrolytic bath until the frame 12 is immersed in the electrolytic fluid without immersing the motor 18. One example of the type of electrolytic fluid that may be used is a mixture of sulfuric and phosphoric acids. However, any common electrolytic fluid may be used. The swing arm 24 is then rotated upward so that the anode wire 20 rises out of the electrolytic bath. Next, a stent 34 is placed on the anode wire 20 by sliding the stent 34 down over the anode wire 20, with the wire 20 extending through the cylindrical cavity of the stent 34. The swing arm 24 is then rotated back down into the electrolytic bath.

The electropolishing operation is started by operating the motor 18 at the same time that a voltage is applied across the anode 20 and the cathode 28. The motor 18 rotates the roller 14, which in turn rotates the stent 34. The bottom end of the stent 34 rotates on the bottom of the swing arm 24, which provides a smooth rotational surface to avoid catching the end of the stent 34 during rotation. The longitudinal grooves 16 in the outer surface of the roller 14 assist rotation of the stent 34 by providing additional traction, or friction, between the roller 14 and the stent 34. Longitudinal grooves 16 oriented parallel to the rotational axis of the roller 14 have been found to be better than various types of helical grooves since helical grooves or other like features may tend to drive the stent 34 either upward off the anode wire 20 or downward into the swing arm 24. In addition to rotating the stent 34, the roller 14 has the effect of pulling the stent 34 in the direction that the roller 14 is rotating. As a result, the anode wire 20 contacts the inside surface of the stent 34 along the side edge of the anode wire 20, thereby maintaining the position of the stent 34 on the roller 14 while permitting the stent 34 to roll. Preferably, the anode wire 20 extends through the entire length of the stent 34 so that the anode wire 20 contacts the stent 34 along a line across the full length of the stent 34.

Accordingly, an electrical contact is established between the anode wire 20 and the stent 34. Since the stent 34 rotates during the electropolishing operation, the electrical contact between the anode wire 20 and the stent 34 continuously changes. In a typical electropolishing operation of an endovascular stent 34, an electrical voltage of about 2 to 6 volts is applied across the anode 20 and the cathode 28 until a satisfactory polish is achieved. In addition, the stent 34 is rotated about 35 revolutions per minute during the electropolishing operation. A rotational speed between about 5 revolutions per minute and 60 revolutions per minute may also provide improved electropolishing results. In addition, the electrolytic bath is heated to about 60° Celsius during the electropolishing operation. As those in the art now recognize, the current density applied to the stent 34 causes metal to be removed from the stent 34. The charged metal particles are then drawn through the electrolytic fluid to the cathode loops 30. The removal of metal from the stent 34 results in a smooth polishing effect, with any burrs and sharp edges being removed at a faster rate than the smooth surfaces of the stent 34.

In order to achieve more consistent polishing from part to part, the polishing method is controlled through the use of an amp-hour meter 36, which measures the amount of electrons that pass through the circuit. Thus, the amp-hour meter 36 provides a more repeatable polish by adjusting the amount of time the stent 34 is polished if contact between the anode 20 and the stent 34 becomes intermittent due to the changing contact point. Therefore, the method may be controlled by establishing a specific cumulative current flow instead of relying upon a set amount of polishing time (which may result in inconsistent polishing from one medical implant to another).

The advantages of the electropolishing apparatus and method are numerous.

One of the significant advantages is that the generation of marks around an electrical contact between the anode 20 and the stent 34 are eliminated and/or minimized. In conventional electropolishing apparatuses, these marks appear as an irregular pattern of small grooves or pits. However, by rotating the stent, and constantly changing the electrical contact, the described apparatus 10 spreads the average current density more evenly around the stent 34, thereby preventing the high current density near the anode 20 from concentrating on a single area of the stent 34. Likewise, the area of the stent that is masked by the anode 20 is constantly moved so that any particular area of the stent 34 experiences only a momentary masking effect as the electrical contact moves around the stent 34. As a result, the electrical contact of the described apparatus 10 acts like an infinitely variable electrical contact in contrast to conventional static or periodic electrical contacts. Thus, compared to conventional electropolishing apparatuses and methods, stents 34 and other medical devices may be polished with improved surface finishes by eliminating the marks associated with the anode-stent electrical contact that are common with conventional systems.

Another significant advantage of the electropolishing apparatus 10 is that the metal removal rate across the entire stent 34 is more uniform than with conventional electropolishing systems. Uneven polishing is a common cause of manufacturing rejects. As those in the art well know, the dimensions of a stent 34 must be closely monitored to ensure that the stent 34 will function in a reliable manner. One physical dimension that is closely monitored is the width of the struts of the stent 34. In some prior art apparatuses, electropolishing has been so uneven that the width of the struts at the ends of the stent is significantly thinner than the width of the struts in the middle of the stent. The described apparatus and method overcome this problem in part by continuously rotating the stent 34. As a result, the distance between the cathode and any given point on the stent 34 continuously changes. In effect, the distance between the stent 34 and the cathode 28 is averaged for all points on the stent 34. Thus, the metal removal rate is equalized. In addition, the cathode 28 is made up of three cathode loops 30 that are equally spaced apart from each other. Thus, the distance between the cathode loops 30 and the stent 34 is further averaged and equalized. Therefore, it is apparent that the electropolishing apparatus 10 may reduce expenses and improve the quality of stents 34 by reducing manufacturing rejects and minimizing polishing variations.

The location and design of the anode 20 also offer several advantages. Since the anode 20 is made from a relatively small diameter wire 20, the anode wire 20 only fills a part of the cylindrical interior volume of the stent 34. This allows more electrolytic fluid into the center region than is possible with some prior art apparatuses that use larger diameter stems that extend through the center of the stent. The greater amount of electrolytic fluid in the center region further facilitates consistent, even electropolishing. Although the wire diameter used in the described apparatus is about 0.025 inch, a wire diameter as large as 75% of the inner diameter of the stent may provide similar advantages.

The constant rotation of the stent 34 also has the effect of circulating the electrolytic fluid during electropolishing. This also facilitates a more consistent polishing effect. In particular, the stent structure itself (i.e., the struts and openings of the stent 34) stirs the electrolytic fluid as the stent 34 rotates. Thus, electrolytic fluid continuously flows around and inside the stent 34. As mentioned above, the small diameter anode wire 20 permits a significant amount of electrolytic fluid into the center region as well. The benefit of this design is that the electrolytic fluid in the center region is also circulated and mixed as the stent 34 rotates.

Another advantage of the anode wire 20 is that it contacts the stent 34 on the inside surface of the stent 34. Thus, the electric current flows between the inner surface of the stent 34 (i.e., where the anode 20 contacts the stent 34) and the outer surface of the stent 34 (i.e., the closest surface to the cathode 28). This provides a more consistent current density across the entire stent 34, which again results in more even polishing.

The small diameter anode wire 20 has other advantages as well. One advantage is that the cost of the electropolishing apparatus 10 may be reduced. As those in the art well know, platinum is an especially expensive material. Thus, by making the anode 20 out of a small diameter wire 20, the amount of platinum is reduced and the cost of the apparatus 10 is minimized. In contrast, other arrangements may be used that also constantly rotate the stent 34 and continuously change the anode-stent contact, such as using a large anode roller which contacts the outer surface of the stent or placing the stent in a rotating anode drum. However, these possible alternatives would greatly increase the amount of platinum, or other anode material, that would be needed, thereby increasing the cost of the apparatus 10. Furthermore, a small anode is generally desired during electropolishing operations in order to obtain an accurate reading of the amount of metal removed. (The larger the anode, the less accurate the reading). Thus, the small diameter anode wire 20 has the advantage of enabling accurate metal removal measurements during the electropolishing operation compared to other alternatives.

The orientation of the roller 14 and the design of the swing arm 24 also offer advantages. The angled roller 14 prevents the stent 34 from walking off the roller 14 as might happen if the roller 14 were oriented horizontally. Moreover, the non-vertical orientation allows the stent 34 to rest on top of the roller 14, thereby generating rotational friction to roll the stent 34. In addition, the swing arm 24 may be rotated upward and out of the electrolytic bath while leaving the roller 14 and the motor 18 permanently mounted in place. This makes loading and unloading stents 34 quicker and easier. To unload a stent 34, the swing arm 24 may be rotated upward by hand without having to contact the electrolytic bath. In fact, the swing arm 24 may be rotated 180° or more until the free end 22 of the anode wire 20 is pointing downward and away from the frame 12 of the electropolishing apparatus. The polished stent 34 will then slide off the anode wire 20 by itself and may be allowed to drop into a collection bin. To load a new stent 34 that is to be polished, the swing arm 24 is simply rotated so that the anode wire 20 is located above the electrolytic bath with the free end 22 of the anode wire 20 pointing upward. The stent 34 is then mounted on the anode wire 20 by sliding the stent 34 down the wire 20. The swing arm 24 may then be rotated back down into the electrolytic bath.

Accordingly, it is now apparent that there are many advantages of the invention provided herein. In addition to the many advantages that have been described, it is possible that there are other advantages that are not currently recognized but which may become apparent at a later time.

While a preferred embodiment of the invention has been described, it should be understood that the invention is not so limited, and modifications may be made without departing from the invention. The scope of the invention is defined by the appended claims, and all devices that come within the meaning of the claims, either literally or by equivalence, are intended to be embraced therein.

I claim:

1. An apparatus for electro-polishing a medical implant, comprising:
    an anode adapted to contact a surface of said medical implant, thereby establishing an electrical contact between said anode and said medical implant;
    a roller operably driven by a motor and contacting said medical implant, said roller thereby being adapted to continuously rotate said medical implant;
    a cathode spaced away from said anode;
    wherein said electrical contact between said anode and said medical implant continuously changes as an electrical voltage is applied across said anode and said cathode and said roller is rotated by said motor, said medical implant thereby being electro-polished while minimizing the generation of marks on said medical implant at said electrical contact; and
    wherein said cathode comprises at least two cathodes elements, each of said cathode elements defining a loop wherein said loops are spaced apart from each other.

2. An apparatus for electro-polishing a medical implant, comprising:
    an anode adapted to contact a surface of said medical implant, thereby establishing an electrical contact between said anode and said medical implant;
    a roller operably driven by a motor and contacting said medical implant, said roller thereby being adapted to continuously rotate said medical implant;
    a cathode spaced away from said anode;
    wherein said electrical contact between said anode and said medical implant continuously changes as an electrical voltage is applied across said anode and said cathode and said roller is rotated by said motor, said medical implant thereby being electro-polished while minimizing the generation of marks on said medical implant at said electrical contact; and
    wherein said anode is attached to a swing arm, said swing arm adapted to lift said anode and medical implant out of an electrolytic bath while leaving said roller and said cathode immersed in said electrolytic bath.

3. An apparatus for electro-polishing a stent, comprising:
    an anode adapted to contact an inner surface of said stent, thereby establishing an electrical contact between said anode and said stent;
    a roller adapted to contact an outer surface of said stent, said roller being made of a non-conductive material;
    a motor operably driving said roller, said roller thereby being adapted to continuously rotate said stent;
    a cathode spaced away from said anode;
    wherein said electrical contact between said anode and said stent continuously changes as an electrical voltage is applied across said anode and said cathode and said roller is rotated by said motor; and
    wherein said cathode comprises at least two cathode elements, each of said cathode elements defining a loop wherein said loops are spaced apart from each other.

4. An apparatus for electro-polishing a stent, comprising:
    an anode adapted to contact an inner surface of said stent, thereby establishing an electrical contact between said anode and said stent;
    a roller adapted to contact an outer surface of said stent, said roller being made of a non-conductive material;
    a motor operably driving said roller, said roller thereby being adapted to continuously rotate said stent;
    a cathode spaced away from said anode;
    wherein said electrical contact between said anode and said stent continuously changes as an electrical voltage is applied across said anode and said cathode and said roller is rotated by said motor; and
    wherein said anode is attached to a swing arm, said swing arm adapted to lift said anode and stent out of an electrolytic bath while leaving said roller and said cathode immersed in said electrolytic bath.

5. An apparatus for electro-polishing a stent, comprising:
    an anode adapted to contact an inner surface of said stent, thereby establishing an electrical contact between said anode and said stent;
    a roller adapted to contact an outer surface of said stent, said roller being made of a non-conductive material;
    a motor operably driving said roller, said roller thereby being adapted to continuously rotate said stent;
    a cathode spaced away from said anode;
    wherein said electrical contact between said anode and said stent continuously changes as an electrical voltage is applied across said anode and said cathode and said roller is rotated by said motor; and
    wherein said roller is oriented at an angle between a horizontal orientation and a vertical orientation; and said anode is attached to a swing arm, said swing arm adapted to lift said anode and stent out of an electrolytic bath while leaving said roller and said cathode immersed in said electrolytic bath.

6. An apparatus for electro-polishing a stent, comprising:
    an anode adapted to contact an inner surface of said stent, thereby establishing an electrical contact between said anode and said stent;
    a roller adapted to contact an outer surface of said stent, said roller being made of a non-conductive material;
    a motor operably driving said roller, said roller thereby being adapted to continuously rotate said stent;
    a cathode spaced away from said anode;
    wherein said electrical contact between said anode and said stent continuously changes as an electrical voltage is applied across said anode and said cathode and said roller is rotated by said motor; and
    wherein said anode extends along an entire length of said stent; said anode is a wire with a diameter 75% or less than an inner diameter of said stent; said anode is made from platinum and said cathode is made from a same material as said stent; said roller comprises grooves extending longitudinally thereon, said grooves thereby driving said stent as said roller rotates; said roller is oriented at an angle between a horizontal orientation and a vertical orientation; and said anode is attached to a swing arm, said swing arm adapted to lift said anode and stent out of an electrolytic bath while leaving said roller and said cathode immersed in said electrolytic bath.

* * * * *